US012766138B2

(12) United States Patent
Cohen

(10) Patent No.: US 12,766,138 B2
(45) Date of Patent: *Oct. 20, 2026

(54) METHODS AND COMPOSITIONS FOR TREATING VIRAL INFECTIONS WITH DOUBLE AND TRIPLE COMBINATIONS OF ANTIVIRAL AND IMMUNE MODULATING COMPOUNDS

(71) Applicant: IATERION, INC., Oakland, CA (US)

(72) Inventor: Isaac Cohen, Oakland, CA (US)

(73) Assignee: Iaterion, Inc., Oakland, CA (US)

( * ) Notice: Subject to any disclaimer, the term of this patent is extended or adjusted under 35 U.S.C. 154(b) by 651 days.

This patent is subject to a terminal disclaimer.

(21) Appl. No.: 18/026,568

(22) PCT Filed: Sep. 15, 2021

(86) PCT No.: PCT/US2021/050504

§ 371 (c)(1),
(2) Date: Mar. 15, 2023

(87) PCT Pub. No.: WO2022/060865

PCT Pub. Date: Mar. 24, 2022

(65) Prior Publication Data

US 2023/0310414 A1 Oct. 5, 2023

Related U.S. Application Data

(60) Provisional application No. 63/211,769, filed on Jun. 17, 2021, provisional application No. 63/211,779, filed on Jun. 17, 2021, provisional application No. 63/211,741, filed on Jun. 17, 2021, provisional application No. 63/211,694, filed on Jun. 17, 2021, provisional application No. 63/211,701, filed on Jun. 17, 2021, provisional application No. 63/079,849, filed on Sep. 17, 2020, provisional application No. 63/079,861, filed on Sep. 17, 2020.

(51) Int. Cl.

| | |
|---|---|
| ***A61K 31/4745*** | (2006.01) |
| ***A61K 31/7034*** | (2006.01) |
| ***A61P 31/14*** | (2006.01) |

(52) U.S. Cl.

CPC ...... *A61K 31/4745* (2013.01); *A61K 31/7034* (2013.01); *A61P 31/14* (2018.01)

(58) Field of Classification Search

None

See application file for complete search history.

(56) References Cited

U.S. PATENT DOCUMENTS

| | | | |
|---|---|---|---|
| 6,123,943 | A | 9/2000 | Baba et al. |
| 8,242,144 | B2 | 8/2012 | Wong et al. |
| 9,445,600 | B2 | 9/2016 | Bui et al. |
| 2011/0190325 | A1 | 8/2011 | Hammond et al. |
| 2014/0275139 | A1 | 9/2014 | Van Dyke |
| 2018/0303823 | A1 | 10/2018 | Bauta et al. |

FOREIGN PATENT DOCUMENTS

| | | | |
|---|---|---|---|
| KR | 100988877 | B1 | 10/2010 |
| WO | 2006127539 | A1 | 11/2006 |
| WO | 2021154687 | A1 | 8/2021 |

OTHER PUBLICATIONS

Fielding BC, da Silva Maia Bezerra Filho C, Ismail NS, Sousa DP. Alkaloids: therapeutic potential against human coronaviruses. Molecules. Jan. 2020;25(23):5496.*

Jo et al., Characteristics of Flavonoids as potent MERS-CoV 3C-like protease inhibitors, Chemical Biology & Drug Design, Aug. 22, 2019 (Aug. 22, 2019) vol. 94, p. 2023-2030; p. 2023, abstract, p. 2026, Figure 1.

International Search Report for PCT/US21/50436 date of mailing Feb. 4, 2022.

Kim et al., Natural Bis-Benzylisoquinoline Alkaloids-Tetrandrine, Fangchinoline, and Cepharanthine, Inhibit Human Coronavirus OC43 infection of MRC-5 Human Lung Cells, Biomolecules 2019, 9, 696, pp. 1-16, entire document especially abstract, Figure 2, p. 12, para 2, Figure 7B.

International Search Report for PCT/US21/50504 date of mailing Feb. 9, 2022.

* cited by examiner

*Primary Examiner* — Patrick T Lewis

(74) *Attorney, Agent, or Firm* — Young Basile Hanlon & MacFarlane, P.C.

(57) ABSTRACT

Antiviral compounds, compositions and method are presented. The composition comprises a first antiviral compound and a second antiviral compound, as described herein, optionally a third antiviral compound, as described herein, and an excipient. The excipient may be pharmaceutically acceptable. The excipient may comprise at least one compound that does not occur naturally with a combination of antiviral compounds as described herein in nature. The method comprises administering a pharmaceutical composition comprising a combination of antiviral compounds as described herein and a pharmaceutically acceptable excipient to a patient who has, is suspected of having, or is susceptible to a viral infection.

5 Claims, 7 Drawing Sheets

FIG. 1: Percent Maximum Inhibition versus Tetrandrine Concentration
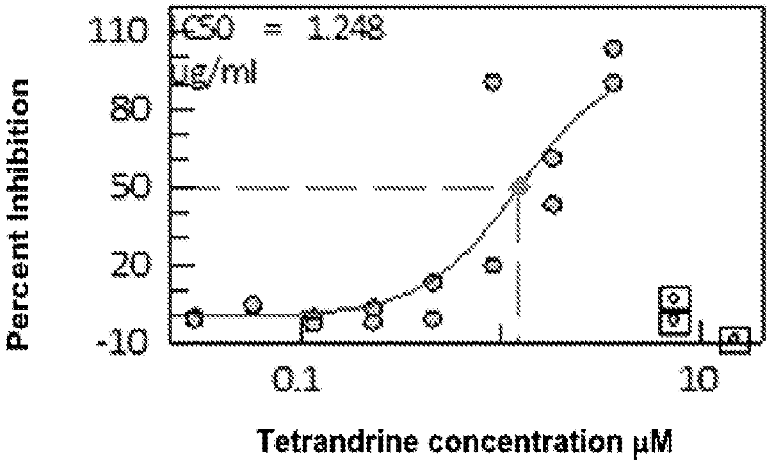
FIG. 2: Tetrandrine Toxicity
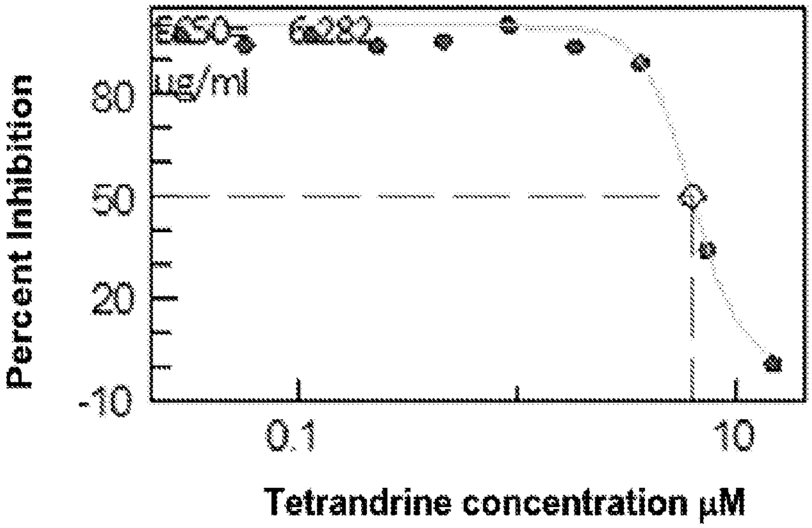

FIG. 3: Percent Maximum Inhibition versus Cepharanthine Concentration
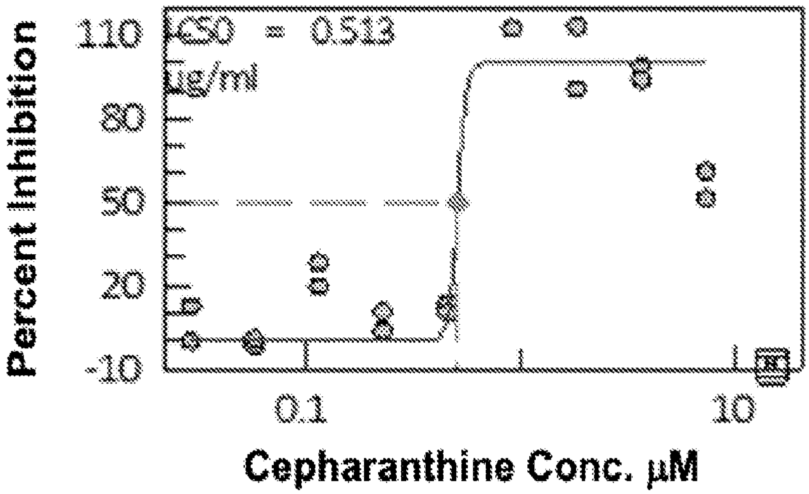
FIG. 4: Cepharanthine Toxicity
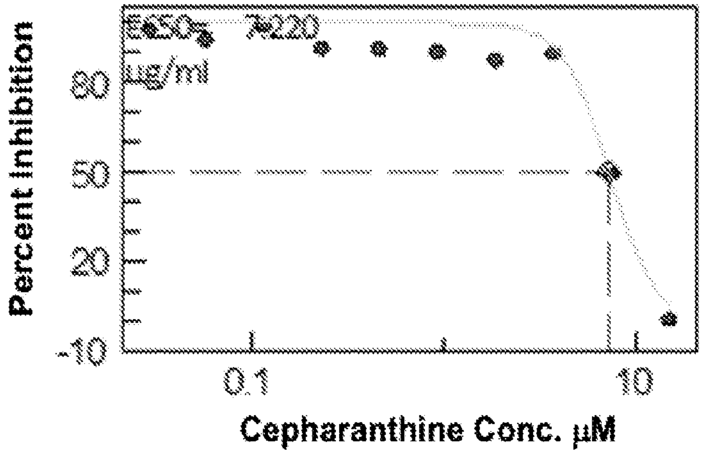

METHODS AND COMPOSITIONS FOR TREATING VIRAL INFECTIONS WITH DOUBLE AND TRIPLE COMBINATIONS OF ANTIVIRAL AND IMMUNE MODULATING COMPOUNDS

CROSS REFERENCE TO RELATED APPLICATIONS

This application claims priority under 35 U.S.C. § 119(e) to U.S. Provisional Patent Applications 63/079,849, 63/079,861, each filed Sep. 17, 2020, and each incorporated herein in its entirety. This application also claims priority under 35 U.S.C. § 119(e) to U.S. Provisional Patent Applications 63/211,741, 63/211,694, 63/211,701, 63/211,769 and 63/211,779, each filed Jun. 17, 2021, and each incorporated herein in its entirety.

FIELD

The present invention is directed to antiviral compounds, compositions, and methods, including compositions for use in the antiviral and/or immune modulating treatment of a patient having a viral infection.

BACKGROUND

The current COVID-19 pandemic underscores the continuing need for antiviral therapies to address viral infections caused by known and emergent viruses. COVID-19 is caused by the emergent virus, SARS-CoV-2, a novel coronavirus first identified in human populations in 2019. While preventative measures, such as social distancing, masking, and vaccines may be helpful in attenuating the rate of spread of the virus through a population, many of these measures, and especially vaccination, are considered controversial and their acceptance in the general population has been uneven. Despite vaccine manufacturers' claims that vaccines confer high degrees of immunity, vaccines provide only partial, and apparently temporary, immunity. Even among the vaccinated population, breakthrough infection is possible, especially with variants, such as the especially transmissible delta variant. Other emergent variants are expected and may be inevitable. It is currently impossible to estimate whether, and to what degree, existing vaccines may be effective in preventing or slowing transmission of newly emergent variants of SARS-CoV-2.

Compounding the need for antiviral therapeutics, the origins of SARS-CoV-2 remain to be determined. While the scientific consensus appears to be that the original SARS virus emerged through exposure of miners in Western China to a bat vector, virologists and epidemiologists have yet to agree on the origins of SARS-CoV-2, though various origins have been posited. Definitive proof of its origins may never materialize. Most importantly, when another emergent virus may cause another global pandemic cannot be predicted with any certainty. Given these uncertainties, additional therapeutic options are needed to counter infections of known and emergent viruses, such MERS, SARS, and SARS-CoV-2 and variants and mutants thereof, not to mention perennial influenza and related viruses.

Several antiviral therapeutics have been developed against HIV; and there are a few options for influenza. However, antiviral therapeutic options remain extremely limited for coronaviruses. Recently, the United States Food and Drug Administration (FDA) granted approval of remdesivir for treatment of COVID-19 in hospitalized patients meeting certain other criteria. Despite continued interest in the field, to date, remdesivir is the only antiviral drug approved for treatment of COVID-19. Additional antiviral options are needed for treating coronavirus infections.

In a significant subpopulation of patients infected with SARS-CoV-2, the infection is characterized by severe acute respiratory syndrome. Significant at-risk populations included older and immune compromised patients, as well as those having one or more comorbidities, such as asthma, obesity, diabetes, high blood pressure, atrial fibrillation, and other heart and lung ailments. More recent variants, however, in addition to being more transmissible, also cause severe acute respiratory disease in broader categories of patients, including some who have been previously infected with, or vaccinated against, the original SARS-CoV-2 virus. This has led to intensified interest in additional antiviral strategies.

One key to a successful pharmaceutical treatment may be found in the viral host's immune system, since more lethal forms of the disease are characterized by a runaway immune response or so-called "cytokine storm." In many viral infections the antiviral cytokine Interferon acts not only to control viral infections, but also to program the adaptive immune response to promote viral clearance. However, in patients with preexisting conditions, as well as in patients with severe COVID-19 disease, aberrant interferon and cytokine responses were observed, delaying onset of symptoms and providing evidence that COVID-19 is an innate immune regulated disease.

Innate immune signaling is the earliest program that alerts host cells to the presence of invading viruses. Pattern Recognition Receptors (PRRs), such as the RIG-1-Like Receptors (RLRs) and Toll-Like Receptors (TLRs), recognize Pathogen Associated Molecular Patterns (PAMPs) from viral components or viral replication intermediates. This recognition results in signaling cascades that initiate an antiviral state in cells. PRRs are distributed on plasma membranes, endosomal membranes, and within the cytosol of host cells to ensure maximal detection of viral PAMPs.

Macrophages are the immune cells in the front line of the body's response to viral infections. There are two kinds of macrophages; those that induce inflammation and those that moderate inflammatory damage. Macrophages neutralize bacteria and viruses using a process called phagocytosis, which engulfs and neutralize the microbes. Macrophages also release chemical signals that trigger an immune response, while at the same time promote tissue homeostasis and regeneration. The SARS-CoV-2 Spike (S) protein is used for the attachment of the virus to the target cell in the host and thus provides a useful PAMP for in vitro antiviral drug discovery and validation experiments involving one or more elements of the innate immune system.

There is a need for additional and novel antiviral therapeutic compositions for treatment of viral infections. There is also a need for antiviral therapeutic compositions that modulate the innate immune system. The various embodiments disclosed herein address these needs and provide related advantages as well.

BRIEF SUMMARY OF THE INVENTION

Described herein are antiviral compositions and methods. In some embodiments, there are provided antiviral compositions comprising a combination of antiviral compounds as described herein, and optionally one or more additional ingredients. In some embodiments, there are provided antiviral compositions comprising a combination of antiviral compounds as described herein and one or more pharmaceutically acceptable ingredients. In some embodiments, the compositions may be oral compositions, intranasal compositions, intrapulmonary compositions (e.g., for inhalation), intravenous compositions, subcutaneous compositions, transdermal, sublingual compositions, buccal compositions, intraperitoneal compositions, intrathecal compositions or intracerebroventricular compositions. In some embodiments, a combination of antiviral compounds as described herein may be in the form of a free molecule or an acid-addition salt. In some embodiments, the combination of antiviral compounds may comprise a combination of tetrandrine, or an antiviral derivative, ester, salt, hydrate, anhydrate, polymorph or tautomer thereof, and cepharanthine, or an antiviral derivative, ester, salt, hydrate, anhydrate, polymorph, or tautomer thereof. In some embodiments, the combination of antiviral compounds may comprise a combination of tetrandrine, or an antiviral derivative, ester, salt, hydrate, anhydrate, polymorph, or tautomer thereof, and cepharanthine, or an antiviral derivative, ester, salt, hydrate, anhydrate, polymorph or tautomer thereof, and penta-O-galloyl-β-D-glucose hydrate or an antiviral derivative, ester, salt, hydrate, anhydrate, polymorph, or tautomer thereof.

Described herein are antiviral methods. In some embodiments, there are provided antiviral methods comprising administration a combination of antiviral compounds as described herein, and optionally one or more pharmaceutically acceptable ingredients to a patient in need thereof. In some embodiments, there are provided antiviral methods comprising administration a composition comprising a combination of antiviral compounds as described herein and one or more pharmaceutically acceptable ingredients to a patient in need thereof. In some embodiments, the methods comprise administering a composition comprising a combination of antiviral compounds as described herein and a pharmaceutically acceptable ingredient orally, intranasally, to the lungs by inhalation, intravenously, transdermally, subcutaneously, sublingually, buccally, or by intraperitoneal or intrathecal injection. Pharmaceutically acceptable ingredients may include one or more additional antiviral compounds that directly inhibit or kill virus, block or inhibit entry of virus into host cells, block or inhibit viral replication, or a combination thereof. Pharmaceutically acceptable ingredients may include one or more compounds that directly inhibit or kill the virus, inhibit or block viral infiltration into host cells, inhibit or block viral replication, or a combination thereof. In some embodiments, the combination of antiviral compounds may comprise a combination of tetrandrine, or an antiviral derivative, ester, salt, hydrate, anhydrate, polymorph, or tautomer thereof, and cepharanthine, or an antiviral derivative, ester, salt, hydrate, anhydrate, polymorph, or tautomer thereof. In some embodiments, the combination of antiviral compounds may comprise a combination of tetrandrine, or an antiviral derivative, ester, salt, hydrate, anhydrate, polymorph, or tautomer thereof, and cepharanthine, or an antiviral derivative, ester, salt, hydrate, anhydrate, polymorph, or tautomer thereof, and penta-O-galloyl-β-D-glucose hydrate or an antiviral derivative, ester, salt, hydrate, anhydrate, polymorph, or tautomer thereof.

The compositions described herein have in vitro antiviral and immune modulating activity in the presence of SARS-CoV-2, and are expected to have similar activity in the presence of other coronaviruses (including SARS-CoV, MERS, and common cold viruses) as well as Influenza A and Influenza B. The methods described herein may be used therapeutically to treat viral infections. The methods described herein may be particularly helpful in the treatment of virus-infected patients who are experiencing one or more symptoms of viral infection, such as one or more symptoms associated with a cytokine storm.

As described herein, tetrandrine is an antiviral compound that selectively induces apoptosis in the SARS-CoV-2 Spike (S) protein treated human macrophages, by activation of caspase 3, within 2 hours of treatment. Tetrandrine selectively inhibited pro-inflammatory cytokine, such as VEGF, IL-6, IL-8, MIP-1a and MIP-1β, while inducing anti-inflammatory cytokines, such as IL-10, in SARS-CoV-2 Spike (S) protein treated human macrophages within 2 hours of treatment, and induced apoptosis in SARS-CoV-2 Spike (S) protein infected human macrophages through caspase 3 induction.

As described herein, cepharanthine is an antiviral compound that selectively induces apoptosis in the SARS-CoV-2 Spike (S) protein treated human macrophages, by activation of caspase 3, within 2 hours of treatment. Cepharanthine selectively inhibited pro-inflammatory cytokine, such as VEGF, IL-6, IL-8, GRO, MIP-1a, MIP-1β and MMP-9 while inducing anti-inflammatory cytokines such as IL-10, in SARS-CoV-2 Spike (S) protein treated human macrophages within 2 hours of treatment. These results indicate that the antiviral compounds enhance type 1 interferon activation, while inhibiting pro-inflammatory cytokine activation and release.

As described herein, penta-O-galloyl-β-D-glucose hydrate is an immune modulator that selectively induces apoptosis in the SARS-CoV-2 Spike (S) protein treated human macrophages, by activation of caspase 3, within 2 hours of treatment. Penta-O-galloyl-β-D-glucose hydrate selectively inhibited pro-inflammatory cytokine, such as IL-1α, VEGF, IL-1β, IL-2, IL-4, IL-5, IL-6, IL-8, IL-12p70, IL-13, GM-CSF, GRO, MCP-1, MIP-1α, MIP-1β, MMP-9, RANTES, and TNF-α, while inducing anti-inflammatory cytokines such as IL-10, in the SARS-CoV-2 Spike (S) protein treated human macrophages within 2 hours of treatment. These results indicate that the immune modulators enhance type 1 interferon activation, while inhibiting pro-inflammatory cytokine activation and release.

Thus, as described in more detail herein, there are provided antiviral compositions and methods of treatment, including compositions for antiviral therapy, wherein the compositions comprise at least a first antiviral compound and a second antiviral compound, where the first antiviral compound comprises tetrandrine, including any antiviral derivative, salt, hydrate, anhydrate, polymorph, or tautomer thereof and the second antiviral compound comprises cepharanthine, including any antiviral derivative, salt, hydrate, anhydrate, polymorph, or tautomer thereof. The antiviral compositions may further comprise an immune modulator compound, wherein the immune modulator compound comprises penta-O-galloyl-β-D-glucose hydrate, including any antiviral derivative, salt, hydrate, anhydrate, polymorph, or tautomer thereof.

There are also provided immune modulating compositions and methods of treatment, including compositions for immune modulating and antiviral therapy, wherein the compositions comprise at least a first antiviral compound and a second antiviral compound, where the first antiviral compound comprises tetrandrine, including any antiviral derivative, salt, hydrate, anhydrate, polymorph, or tautomer thereof and the second antiviral compound comprises cepharanthine, including any antiviral derivative, salt, hydrate, anhydrate, polymorph, or tautomer thereof. The antiviral compositions may further comprise an immune modulator compound, wherein the immune modulator compound comprises penta-O-galloyl-β-D-glucose hydrate, including any antiviral derivative, salt, hydrate, anhydrate, polymorph, or tautomer thereof. In some embodiments, the compositions comprise an amount of the first antiviral compound and the second antiviral compound, and optionally the immune modulator compound, sufficient to inhibit a pro-inflammatory cytokine, induce an anti-inflammatory cytokine, or both. In some embodiments, the compositions comprise an amount of the first antiviral compound and the second antiviral compound, and optionally the third antiviral compound, sufficient to inhibit a pro-inflammatory cytokine, such as IL-1α, VEGF, IL-1β, IL-2, IL-4, IL-5, IL-6, IL-8, IL-12p70, IL-13, GM-CSF, GRO, MCP-1, MIP-1α, MIP-1β, MMP-9, RANTES, and TNF-α, while inducing anti-inflammatory cytokines, such as IL-10.

In some embodiments, there are provided methods of inhibiting pro-inflammatory cytokine activation and release, enhancing type 1 interferon activation, or both, and/or inducing anti-inflammatory cytokines, such as IL-10, comprising administering to a patient in need thereof an amount the first antiviral compound and the second antiviral compound, and optionally the immune modulator compound, sufficient to inhibit pro-inflammatory cytokine activation, release, or both. In some embodiments, there are provided antiviral and immune modulating compositions for use in methods of inhibiting pro-inflammatory cytokine activation and release, enhancing type 1 interferon activation, or both, inducing anti-inflammatory cytokines, or both, wherein the methods comprise administering to a patient in need thereof an amount of the first antiviral compound and the second antiviral compound, and optionally the immune modulator compound, sufficient to inhibit pro-inflammatory cytokine activation, release, or both, and/or induce anti-inflammatory cytokine activation. In some embodiments, the inhibited cytokine may comprise one or more of IL-1α, VEGF, IL-1β, IL-2, IL-4, IL-5, IL-6, IL-8, IL-12p70, IL-13, GM-CSF, GRO, MCP-1, MIP-1α, MIP-1β, MMP-9, RANTES, and TNF-α, and the induced anti-inflammatory cytokine may be IL-10.

Other uses and advantages of the various embodiments described herein will be apparent to those skilled in the art upon review of the following disclosure.

BRIEF DESCRIPTION OF THE DRAWINGS

The features and advantages of the present invention will become apparent from a consideration of the following detailed description presented in connection with the accompanying drawings in which:

FIG. 1 is a dose-response curve for tetrandrine in VERO-E6 cells enriched in ACE-2 receptor and infected with SARS-CoV-2 virus.

FIG. 2 is a dose-toxicity curve for tetrandrine in uninfected VERO-E6 cells.

FIG. 3 is a dose-response curve for cepharanthine in VERO-E6 cells enriched in ACE-2 receptor and infected with SARS-CoV-2 virus.

FIG. 4 is a dose-toxicity curve for cepharanthine in uninfected VERO-E6 cells.

DETAILED DESCRIPTION OF THE INVENTION

Figure 5:
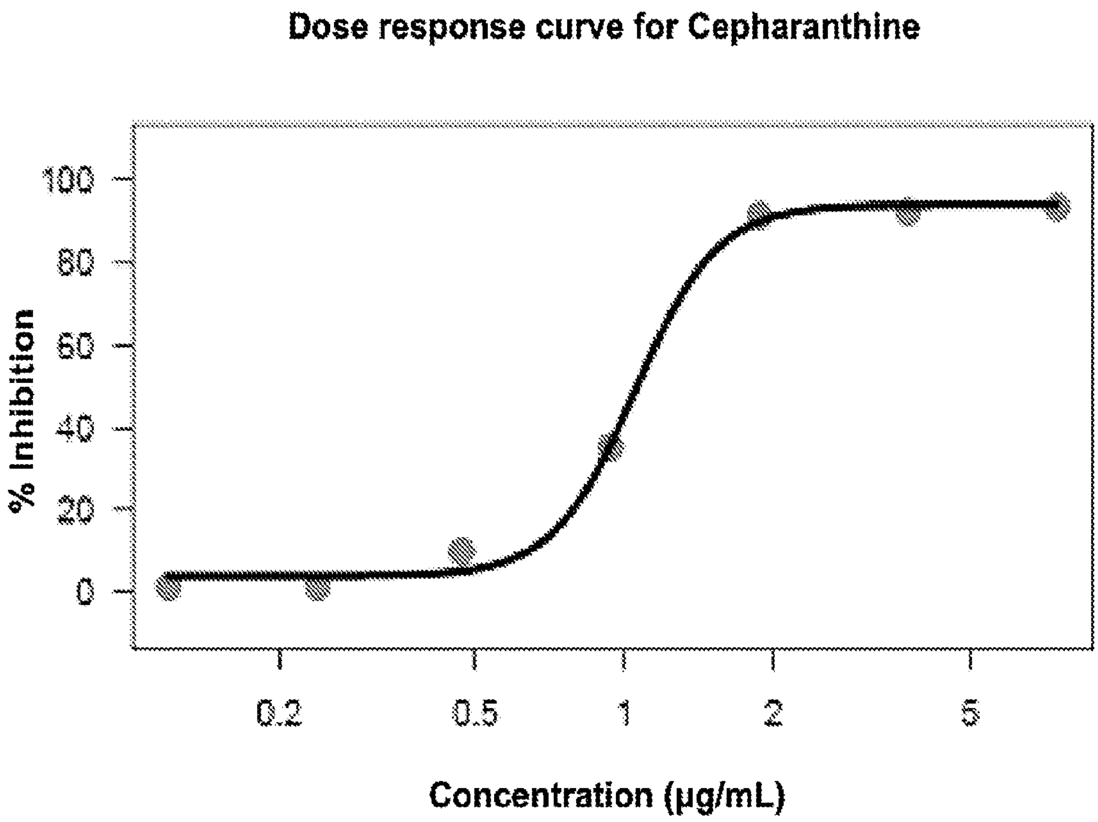
FIG. 5 is a dose-response curve for tetrandrine in VERO-E6 cells enriched in ACE-2 receptor and infected with SARS-CoV-2 virus.

Described herein are compositions of tetrandrine and cepharanthine, including pharmaceutical compositions comprising tetrandrine and cepharanthine, as described herein, and optionally one or more pharmaceutically acceptable excipients, as well as antiviral methods of using tetrandrine and cepharanthine as described herein. In some embodiments, the compositions further comprise an immune modulator comprising penta-O-galloyl-β-D-glucose hydrate, as well as antiviral methods of using tetrandrine, cepharanthine, and penta-O-galloyl-β-D-glucose hydrate.

As described herein, tetrandrine is an antiviral compound that selectively induces apoptosis in the SARS-CoV-2 Spike (S) protein treated human macrophages, by activation of caspase 3, within 2 hours of treatment. Tetrandrine also selectively inhibited pro-inflammatory cytokine, such as VEGF, IL-6, IL-8, MIP-1α and MIP-1β, while inducing anti-inflammatory cytokines such as IL-10 in SARS-CoV-2 Spike (S) protein treated human macrophages within 2 hours of treatment, as well as induced apoptosis in SARS-CoV-2 Spike (S) protein infected human macrophages through caspase 3 induction.

Cepharanthine selectively inhibited pro-inflammatory cytokine, such as VEGF, IL-6, IL-8, GRO, MIP-1α, MIP-1β and MMP-9 while inducing anti-inflammatory cytokines such as IL-10 in SARS-CoV-2 Spike (S) protein treated human macrophages within 2 hours of treatment.

These results indicate that the antiviral compounds tetrandrine and cepharanthine enhance type 1 interferon activation, while inhibiting pro-inflammatory cytokine activation and release.

Penta-O-galloyl-β-D-glucose hydrate

As described herein, penta-O-galloyl-β-D-glucose hydrate is an immune modulator that selectively induces apoptosis in the SARS-CoV-2 Spike (S) protein treated human macrophages, by activation of caspase 3, within 2 hours of treatment. Penta-O-galloyl-β-D-glucose hydrate selectively inhibited pro-inflammatory cytokine, such as IL-1α, VEGF, IL-1β, IL-2, IL-4, IL-5, IL-6, IL-8, IL-12p70, IL-13, GM-CSF, GRO, MCP-1, MIP-1α, MIP-1β, MMP-9, RANTES, and TNF-α, while inducing anti-inflammatory cytokines such as IL-10, in the SARS-CoV-2 Spike (S) protein treated human macrophages within 2 hours of treatment. These results indicate that the immune modulator enhances type 1 interferon activation, while inhibiting pro-inflammatory cytokine activation and release.

The adapter protein myeloid differentiation primary response 88 (MyD88), responds to PAMPs signaling on PRRs. MyD88 signaling can lead to the production of pro- or anti-inflammatory cytokines as well as type I interferons. Type 1 interferons are desired in the control of viral infections. Distinct pathways downstream of interleukin 1 receptor (IL-1R) associated kinase (IRAK) family members in association with MyD88 regulate these outputs, and the outcome of signaling can be influenced by the cell type and location of signal initiation.

One skilled in the art will readily recognize that penta-O-galloyl-β-D-glucose hydrate is a solid form of penta-O-galloyl-β-D-glucose and that when penta-O-galloyl-β-D-glucose is dissolved in an aqueous solvent, the solution contains penta-O-galloyl-β-D-glucose as a solute. In aqueous solution, as well as in vivo, penta-O-galloyl-β-D-glucose is the physical form of the solute and is the biologically active form. Additionally, it will be recognized that in solid form penta-O-galloyl-β-D-glucose hydrate may exist with a variable number of waters of hydration. Thus, in the formula penta-O-galloyl-β-D-glucose $xH_2O$, x may be 0 (i.e., penta-O-galloyl-β-D-glucose is anhydrous) or a real number greater than 0. As penta-O-galloyl-β-D-glucose is hygroscopic, the value of x may vary over time for a sample of penta-O-galloyl-β-D-glucose exposed to an ambient atmosphere, especially for a sample of pure penta-O-galloyl-β-D-glucose hydrate (i.e., not combined with one or more stabilizing excipients). One skilled in the art will recognize, however, that the immune modulating moiety in penta-O-galloyl-β-D-glucose hydrate is the penta-O-galloyl-β-D-glucose portion itself—that is, the degree of hydration is not expected to affect the immune modulating nature of penta-O-galloyl-β-D-glucose, though the degree of hydration should be taken into account when preparing formulations containing penta-O-galloyl-β-D-glucose. Thus, wherever penta-O-galloyl-β-D-glucose hydrate is in an aqueous solution (e.g., an in vitro macrophage model, in vivo, in aqueous solutions for oral or parenteral administration, etc.) it is present as penta-O-galloyl-β-D-glucose, whereas in solid form (e.g., in solid unit dosage forms for oral administration), it may be present as the hydrate, which may occur in various degrees of hydration.

Penta-O-galloyl-β-D-glucose hydrate potently reduced the activation of IRAK1, NF-κB, and MAPKs, while increasing expression of IRAK4 in human macrophages through interaction with MyD88. Penta-O-galloyl-β-D-glucose hydrate also inhibited NF-κB translocation into the nucleus. Penta-O-galloyl-β-D-glucose hydrate also suppressed multiple pro-inflammatory cytokines such as IL-1β, TNF-α, IL-6 IL-8, IL-12, MCP-1 and MIP-1α in SARS-CoV-2 Spike (S) protein treated human macrophages, while increasing expression of the anti-inflammatory cytokine IL-10 in nanomolar concentrations, within 2 hours of treatment, without compromising cell viability.

These results indicate that penta-O-galloyl-β-D-glucose enhances type 1 interferon activation, while inhibiting pro-inflammatory cytokine activation and release.

As described herein penta-O-galloyl-β-D-glucose has immune modulating activity in vitro in the presence of SARS-CoV-2, and is expected to have immune modulating activity in the presence of other coronaviruses, such as SARS-CoV, MERS-CoV, common cold coronavirus, as well as influenza viruses, such as influenza A and influenza B. Based on in vitro data, it is possible to enter human clinical trials, as taught in the FDA's Guidance for Industry: Antiviral Product Development-Conducting and Submitting Virology Studies to the Agency (June 2006), which is incorporated herein by reference in its entirety, especially pp. 4-5. See also McMahon et al., "New Approaches for Quantitating the Inhibition of HIV-1 Replication by Antiviral Drugs in vitro and in vivo," Curr. Opin. Infect. Dis. 2009 December; 22(6): 574-582, which is incorporated herein in its entirety.

Penta-O-galloyl-β-D-glucose hydrate has the formula:

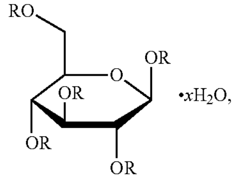

wherein each R is

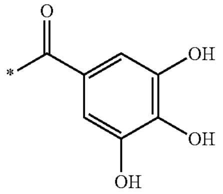 [SMILES: *C(=O)c1cc(O)c(O)c(O)c1]

and x is a real number greater than zero.

The immune modulator penta-O-galloyl-β-D-glucose hydrate may be obtained from commercial sources, such as Millipore-Sigma (www.sigmaaldrich.com).

Tetrandrine

Tetrandrine (IUPAC name (1S,14S)-9,20,21,25-tetramethoxy-15,30-dimethyl-7,23-dioxa-15,30-diazaheptacyclo[$22.6.2.2^{3,6}.1^{8,12}.1^{14,18}.0^{27,31}.0^{22,33}$]hexatriaconta-3(36),4,6(35),8,10,12(34),18,20,22(33),24,26,31-dodecaene) has the chemical structure:

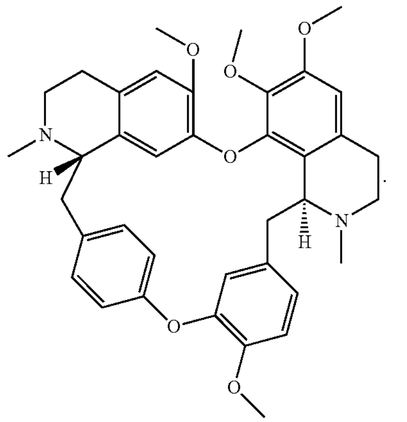 [SMILES: COc1ccc2cc1Oc1ccc(cc1)C[C@H]1c3cc(c(OC)cc3CCN1C)Oc1c(OC)c(OC)cc3c1[C@H](C2)N(C)CC3]

Tetrandrine may be isolated from radix *Stephania tetrandra* and is commercially available from various sources.

Tetrandrine is a proteolytic processing inhibitor of S1/S2 site of the coronavirus spike protein, attaching to the human angiotensin converting enzyme 2 receptor (ACE2) and cepharanthine is an entry inhibitor, which reduces plasma membrane fluidity interfering with the virus' ability to attach to ACE2 receptor, and an RNA synthesis inhibitor, which inhibits viral replication.

Cepharanthine

Cepharanthine (IUPAC name (14S,27S)-22,33-dimethoxy-13,28-dimethyl-2,5,7,20-tetraoxa-13,28-diazaoctacyclo[$25.6.2.2^{16,19}.1^{3,10}.1^{21,25}.0^{4,8}.0^{31,35}.0^{14,39}$]nonatriaconta-1(33),3(39),4(8),9,16(38),17,19(37),21,23,25(36),31,34-dodecaene) has the chemical structure:

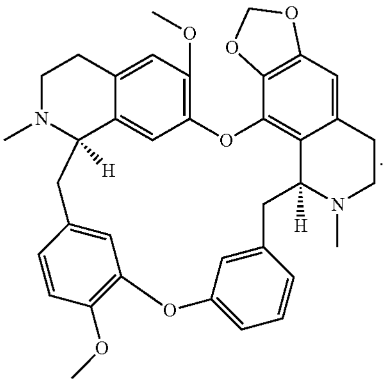 [SMILES: COc1ccc2cc1Oc1cccc(c1)C[C@H]1c3c(cc4c(c3Oc3cc5c(cc3OC)CCN(C)[C@@H]5C2)OCO4)CCN1C]

Cepharanthine is commercially available from various sources.

Cepharanthine selectively inhibited pro-inflammatory cytokines, such as VEGF, IL-6, IL-8, GRO, MIP-1α, MIP-1β and MMP-9 while inducing anti-inflammatory cytokines such as IL-10 in SARS-CoV-2 Spike (S) protein treated human macrophages within 2 hours of treatment. Cepharanthine is an entry inhibitor, reducing plasma membrane fluidity interfering with the virus' ability to attach to ACE2 receptor and RNA synthesis inhibitor, inhibiting viral replication.

These results indicate that tetrandrine and cepharanthine inhibit SARS-CoV-2 viral entry into human cells and inhibit viral replication, thereby neutralizing SARS-CoV-2 infection, while also enhancing type 1 interferon activation and inhibiting pro-inflammatory cytokine activation and release.

As described herein combinations of tetrandrine and cepharanthine have antiviral properties as well as immune modulating activity in vitro in the presence of SARS-CoV-2, and are expected to have antiviral and immune modulating activity in the presence of other coronaviruses, such as SARS-CoV, MERS-CoV, common cold coronavirus, as well as influenza viruses, such as influenza A and influenza B. Based on in vitro data, it is possible to enter human clinical trials, as taught in the FDA's Guidance for Industry: Antiviral Product Development—Conducting and Submitting Virology Studies to the Agency (June 2006), which is incorporated herein by reference in its entirety, especially pp. 4-5. See also McMahon et al., "New Approaches for Quantitating the Inhibition of HIV-1 Replication by Antiviral Drugs in vitro and in vivo," Curr. Opin. Infect. Dis. 2009 December, 22(6): 574-582, which is incorporated herein in its entirety.

It is expected that compounds of the following Formula I will have similar antiviral and immune modulating activity to tetrandrine, based on their structural similarity to tetrandrine, and are thus included within the antiviral and antiviral compounds as described herein.

Formula I

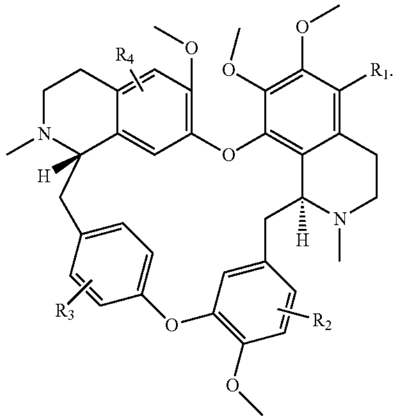

In Formula I, each of $R_1$ $R_2$, $R_3$ and $R_4$ is independently H or a substituent. $R_1$ is H, OH, F, Cl, Br, I, $CH_3$, $CH_2F$, $CHF_2$, or $CF_3$. $R_2$ and $R_3$ are independently H or one to three substituents, independently selected from OH, F, Cl, Br, I, $CH_3$, $CH_2F$, $CHF_2$, or $CF_3$. $R_4$ is H or one to two substituents, independently selected from OH, F, Cl, Br, I, $CH_3$, $CH_2F$, $CHF_2$, or $CF_3$. In some embodiments, at least one of $R_1$ $R_2$, $R_3$ and $R_4$ is a substituent.

Compounds of Formula I in which $R_1$ $R_2$, $R_3$ and $R_4$ is a substituent other than H may be prepared by electrophilic substitution on the aryl ring by adapting art-recognized methods of electrophilic substitution.

The effect of tetrandrine and cepharanthine on cytokine response in human macrophages treated with CoV-2 spike protein was tested. Specifically, the effect of tetrandrine on the expression of IL-1α (interleukin 1 alpha), IL-10 (interleukin 10), IFN-γ, VEGF, IL-1β (interleukin 1 beta), IL-2 (interleukin 2), IL-4 (interleukin 4), IL-5 (interleukin 5), IL-6 (interleukin 6), IL-8 (interleukin 8), IL-12p70 (interleukin 12 p70), IL-13 (interleukin 13), GM-CSF (granulocyte-macrophage colony-stimulating factor), GRO (growth related oncogene protein), MCP-1 (monocyte chemoattractant protein-1), MIP-1α (macrophage Inflammatory Protein 1 alpha), MIP-1β (macrophage Inflammatory Protein 1 beta), MMP-9 (matrix metallopeptidase 9), RANTES (Regulated on Activation, Normal T Cell Expressed and Secreted) and TNF-α (tumor necrosis factor alpha), was detected in vitro.

It is expected that compounds of the following Formula II will have similar antiviral and immune modulating activity to cepharanthine, based on their structural similarity to cepharanthine, and are thus included within the antiviral compound compounds as described herein.

Formula II

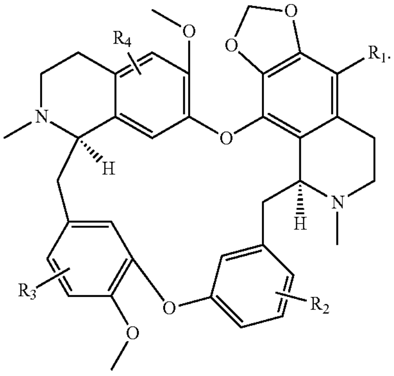

In Formula II, each of $R_5$, $R_6$, $R_7$ and $R_8$ is independently H or a substituent. $R_5$ is H, OH, F, Cl, Br, I, $CH_3$, $CH_2F$, $CHF_2$, or $CF_3$. $R_6$ and $R_7$ are independently H or one to three substituents, independently selected from OH, F, Cl, Br, I, $CH_3$, $CH_2F$, $CHF_2$, or $CF_3$. $R_4$ is H or one to two substituents, independently selected from OH, F, Cl, Br, I, $CH_3$, $CH_2F$, $CHF_2$, or $CF_3$. In some embodiments, at least one of $R_5$, $R_6$, $R_7$ and $R_8$ is a substituent.

Compounds of Formula II in which $R_5$, $R_6$, $R_7$ and $R_8$ is a substituent other than H may be prepared by electrophilic substitution on the aryl ring by adapting art-recognized methods of electrophilic substitution.

Antiviral Activity

As used herein, the term "antiviral" (and its grammatical variants) means that an antiviral compound, composition, or method described herein modulates the immune response of a host infected with a virus, or both to treat one or more symptoms of the viral infection, reduce the host's viral load, or both. Such antiviral activity or immune modulation may be topical, local, or systemic. Antiviral activity may be demonstrated in vitro by demonstrating that an antiviral compound (i.e., tetrandrine, or a compound of Formula I or Formula II, or a pharmaceutically acceptable salt or solvate thereof) as described herein modulates immune response in the presence of a virus, such as a coronavirus (e.g., SARS-CoV, MERS-CoV, SARS-CoV-2, or a common cold coronavirus) or an influenza virus (e.g., Influenza A or Influenza B), or a viral component (e.g., a spike protein of SARS-CoV, MERS-CoV, or SARS-CoV-2) thereof. For example, antiviral activity may be demonstrated in vitro by detecting up- or down-regulation of one or more cytokines in macrophages treated with SARS-CoV-2 Spike protein. Up- or down-regulation of one or more cytokines may be detected in vitro using art-recognized assays, including PCR and Luminex™ methods. One or more symptoms of a viral infection may include one or more symptoms associated with a cytokine storm, such as respiratory failure, severe inflammation of the pulmonary epithelial tissue, over-production of phlegm, severe respiratory distress, reduced pulse oximetry (e.g., less than 90%, less than 85%, or less than 80% blood oxygen saturation), cardiovascular symptoms, such as congestive heart failure, renal failure, neurological pathology, sepsis, or very high or prolonged fever. One or more symptoms of a viral infection may also chills, cough, fatigue, muscle or body aches, headache, loss of taste or smell, sinus congestion, rhinitis, rhinorrhea, nausea, vomiting, or diarrhea. A combination of antiviral compounds as described herein be combined with one or more antiviral therapies. For example, a combination of antiviral compounds as described herein may be combined with one or more pharmaceutical agents that inhibit or kill the virus directly, block or inhibit viral entry into host cells, block or inhibit viral replication, or a combination thereof.

Synergistic Compositions

Tetrandrine and cepharanthine have synergistic antiviral activity in vitro. Specifically, in a CPE assay on VERO-66 cells enriched with ACE2 receptors infected with SARS-CoV-2 virus, tetrandrine and cepharanthine each independently demonstrated potent anti-SARS-CoV-2 activity with low cytotoxicity.

Pharmaceutical Compositions

Pharmaceutical compositions described herein comprise two or more antiviral compounds and one or more pharmaceutically acceptable ingredients. The two or more antiviral compounds may comprise: (1) tetrandrine, or a compound of Formula I, or a pharmaceutically acceptable salt or solvate thereof; and (2) cepharanthine, or a compound of Formula II, or a pharmaceutically acceptable salt or solvate thereof. At least one of the pharmaceutically acceptable ingredients may include ingredients that do not naturally occur with tetrandrine or cepharanthine, a salt or a solvate thereof, in nature. Pharmaceutically acceptable ingredients that do not naturally occur with tetrandrine or cepharanthine, a salt or a solvate thereof, in nature may include sterile, isotonic, or pyrogen free excipients.

A "pharmaceutically acceptable" ingredient is an ingredient that is compatible with the antiviral compounds as described herein and with other ingredients of the composition and is suitable for administration to a patient. Additional ingredients may include carriers, diluents, absorption enhancers, stabilizers, preservatives, or other active or inactive ingredients. At least one of the additional ingredients may be an ingredient that does not occur naturally with a combination of antiviral compounds as described herein in nature. At least one of the additional ingredients may be an ingredient other than water. In some embodiments, the pharmaceutical composition may be sterile, pyrogen free, and/or isotonic. In some embodiments, the pharmaceutical composition is sterile or pyrogen free. In some embodiments, the pharmaceutical composition is sterile and pyrogen free. In some preferred embodiments, the pharmaceutical composition is sterile, pyrogen free and isotonic.

In some embodiments, the pharmaceutical composition may be an antiviral composition. The antiviral composition comprises an antivirally effective amount of a combination of antiviral compounds as described herein and an additional ingredient. The additional ingredient may be an excipient. The excipient may comprise at least one compound that does not occur naturally with an antiviral compound in nature. In particular, the excipient may comprise at least one compound that does not naturally occur with a combination of antiviral compounds as described herein in humans. In some embodiments the excipient may comprise at least one compound other than water. In some embodiments, the additional compound may be a salt or other ingredient at a concentration sufficient for the composition to be isotonic. In some embodiments, the additional ingredient may be a flavor or sweetener not found with a combination of antiviral compounds as described herein in nature. In some embodiments, the antiviral composition may be sterile, pyrogen free, and/or isotonic.

Pharmaceutically acceptable salts may be any salt of an antiviral compound disclosed herein having suitable solubility in an aqueous solvent of appropriate pH. Remington's, 20th Ed., published 2000, pp. 704-719 provides methods for determining appropriate pharmaceutically acceptable salts. For example, suitable salts may be selected from Table 38-2, p. 704 of Remington's. The pharmaceutically acceptable salt may be prepared by dissolving the antiviral compound in a suitable solvent and adding a suitable acid or base, or suitable counter-acid or counter-base, as the case may be, to the solution, and separating the salt form of the antiviral compound from the solution.

Pharmaceutical compositions, in particular antiviral compositions, may be formulated for a variety of routes of administration, such as oral, intranasal, intrapulmonary (e.g., for inhalation), intravenous, subcutaneous, transdermal, sublingual, buccal, intraperitoneal, or intrathecal administration. Pharmaceutical compositions may comprise one or more enhancers to assist in the transport of a combination of antiviral compounds as described herein against one or more external or internal physiological barriers, such as a pulmonary epithelial barrier or a blood brain barrier.

Suitable pharmaceutically acceptable excipients may include the following types of excipients: diluents, lubricants, binders, disintegrants, fillers, glidants, granulating agents, coating agents, wetting agents, solvents, co-solvents, suspending agents, emulsifiers, sweeteners, flavoring agents, flavor masking agents, coloring agents, anti-caking agents, humectants, chelating agents, plasticizers, viscosity increasing agents, antioxidants, preservatives, stabilizers, surfactants, and buffering agents.

Antivirally Effective Doses

The effective dose of a combination of antiviral compounds may vary depending upon a variety of factors, including the route of administration, the age and condition of the patient in need of antiviral treatment, the species and strain of virus, and the severity of viral infection. In general, a combination of antiviral compounds as described herein is effective in vitro at nanomolar or micromolar concentrations. Effective daily doses of a combination of antiviral compounds as described herein may be in the range of 0.01 mg to 1000 mg per day. The effective daily dose may be divided into two or more divided doses, e.g., 1, 2, 3, 4, 5, 6, or more divided doses. Where the antiviral composition is administered as an infusion, the effective daily dose may be administered as a continuous infusion over a course of hours, e.g., 1-24 hours. An effective dose of may be similar to that of a combination of antiviral compounds as described herein, but may be scaled to account for the greater molecular weight of the compared to a combination of antiviral compounds as described herein at the compound's relative bioactivity, pharmacokinetics and pharmacodynamics, which one of skill in the art knows how to determine by art-recognized methods.

One skilled in art of pharmaceutical formulation and compounding possesses the knowledge and skill to select suitable pharmaceutically acceptable carriers and excipients in appropriate amounts for the use with a combination of antiviral compounds as described herein. In addition, there are a number of resources available those skilled in the art, which describe pharmaceutically acceptable carriers and excipients and may be useful in selecting suitable pharmaceutically acceptable carriers and excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

The compositions of antiviral compounds as described herein may be prepared using techniques and methods known to those skilled in the art. Some methods commonly used in the art are described in Remington's Pharmaceutical Sciences, $20^{th}$ Ed., (Mack Publishing Company (2000)).

In some embodiments, antiviral compositions may comprise a combination of antiviral compounds as described herein and one or more pharmaceutically acceptable carriers or excipients. The composition may be prepared and packaged in bulk form wherein an effective amount of a compound of the disclosure can be extracted and then given to a subject, such as with powders or syrups. Alternatively, the composition may be prepared and packaged in unit dosage form wherein each physically discrete unit contains an effective amount of a combination of antiviral compounds as described herein.

A combination of antiviral compounds as described herein, and a pharmaceutically acceptable carrier or excipient(s), may be formulated into a dosage form adapted for administration to a subject by a desired route of administration. For example, dosage forms include those adapted for (1) oral administration, such as tablets, capsules, caplets, pills, troches, powders, syrups, elixirs, suspensions, solutions, emulsions, sachets, and cachets; and (2) parenteral administration, such as sterile solutions, suspensions, and powders for reconstitution. Suitable pharmaceutically acceptable carriers or excipients may vary depending upon the particular dosage form chosen. In addition, suitable pharmaceutically acceptable carriers or excipients may be chosen for a particular function that they may serve in the composition. For example, certain pharmaceutically acceptable carriers or excipients may be chosen for their ability to facilitate the production of uniform dosage forms. Certain pharmaceutically acceptable carriers or excipients may be chosen for their ability to facilitate the production of stable dosage forms. Certain pharmaceutically acceptable carriers or excipients may be chosen for their ability to facilitate the carrying or transporting of a compound disclosed herein, once administered to the subject, from one organ or portion of the body to another organ or another portion of the body. Certain pharmaceutically acceptable carriers or excipients may be chosen for their ability to enhance patient compliance.

In some embodiments, antiviral a combination of antiviral compounds as described herein compositions may be formulated for parenteral administration. Compositions adapted for parenteral administration include aqueous and non-aqueous sterile injection solutions which may contain antioxidants, buffers, bacteriostats, and solutes that render the formulation isotonic with the blood of the intended recipient; and aqueous and non-aqueous sterile suspensions that may include suspending agents and thickening agents. The compositions may be presented in unit-dose or multi-dose containers, for example sealed ampoules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets. Parenteral formulations may be sterile, pyrogen-free, or both. Parenteral formulations may be isotonic.

Oral

The antiviral composition may be an oral antiviral composition comprising a combination of antiviral compounds as described herein and at least one excipient suitable for oral administration. The at least one excipient suitable for oral administration may comprise a compound that does not occur naturally with a combination of antiviral compounds as described herein in nature. The at least one excipient suitable for oral administration may comprise at least one compound other than water. Various dosage forms may be prepared, such as tablets, capsules, caplets, troches, powders, emulsions, sachets, cachets, gel capsules, elixirs, pills, oral sprays, chewable tablets, sublingual tablets, films, or sprays, or buccal films or sprays.

In some embodiments, a combination of antiviral compounds as described herein may be formulated as a solid oral dosage form, such as a tablet or capsule comprising an effective amount of a compound of the disclosure and a diluent or filler. Suitable diluents and fillers include lactose, sucrose, dextrose, mannitol, sorbitol, starch (e.g., corn starch, potato starch, and pre-gelatinized starch), cellulose and its derivatives, (e.g., microcrystalline cellulose), calcium sulfate, and dibasic calcium phosphate. The oral solid dosage form may further comprise a binder. Suitable binders include starch (e.g., corn starch, potato starch, and pre-gelatinized starch) gelatin, acacia, sodium alginate, alginic acid, tragacanth, guar gum, povidone, and cellulose and its derivatives (e.g., microcrystalline cellulose). The oral solid dosage form may further comprise a disintegrant. Suitable disintegrants include crospovidone, sodium starch glycolate, croscarmellose, alginic acid, and sodium carboxymethyl cellulose. The oral solid dosage form may further comprise a lubricant. Suitable lubricants include stearic acid, magnesium stearate, calcium stearate, and talc.

Where appropriate, dosage unit formulations for oral administration can be microencapsulated. The compositions can also be prepared to prolong or sustain the release as, for example, by coating or embedding particulate material in polymers, wax, or the like.

A combination of antiviral compounds as described herein may also be combined with soluble polymers as targetable drug carriers. Such polymers can include polyvinylpyrrolidone, pyrancopolymer, polyhydroxypropylmethacrylamidephenol, polyhydroxyethylaspartam-idephenol, or polyethylene-oxidepolylysine substituted with palmitoyl residues. Furthermore, a combination of antiviral compounds as described herein may be combined with a class of biodegradable polymers useful in achieving controlled release of a drug, for example polylactic acid, polepsilon caprolactone, polyhydroxy butyric acid, polyorthoesters, polyacetals, polydihydropyrans, polycyanacrylates and cross-linked or amphipathic block copolymers of hydrogels.

In some embodiments, a combination of antiviral compounds as described herein may be formulated in a liquid oral dosage form. Oral liquids such as solution, syrups and elixirs can be prepared in dosage unit form so that a given quantity contains a predetermined amount of a compound disclosed herein. Syrups can be prepared by dissolving the compound of the disclosure in a suitably flavored aqueous solution, while elixirs are prepared through the use of a non-toxic alcoholic vehicle. Suspensions can be formulated by dispersing a compound disclosed herein in a non-toxic vehicle. Solubilizers and emulsifiers such as ethoxylated isostearyl alcohols and polyoxy ethylene sorbitol ethers, preservatives, flavor additives such as peppermint oil or other natural sweeteners or saccharin or other artificial sweeteners and the like can also be added.

Intranasal

The antiviral composition may be an intranasal antiviral composition comprising a combination of antiviral compounds as described herein and at least one excipient suitable for intranasal administration. The at least one excipient suitable for intranasal administration may comprise at least one compound other than water. For example, the intranasal antiviral composition may comprise one or more penetration enhancers, which increase absorption of a combination of antiviral compounds as described herein across the mucosa and/or increase bioavailability. In some embodiments, penetration enhancers may include mucolytic agents, degradative enzyme inhibitors and compounds which increase permeability of the mucosal cell membranes. Whether a given compound is an "enhancer" can be determined by comparing two formulations comprising a non-associated, small polar molecule as the drug, with or without the enhancer, in an in vivo or good model test and determining whether the uptake of the drug is enhanced to a clinically significant degree. The enhancer should not produce any problems in terms of chronic toxicity because in vivo the enhancer should be non-irritant and/or rapidly metabolized to a normal cell constituent that does not have any significant irritant effect. In some embodiments, the penetration enhancer may be an alkyl glycoside, e.g., an alkyl glycoside disclosed in U.S. Pat. No. 5,661,130, which is incorporated herein by reference in its entirety. One skilled in the art recognizes the need to achieve a suitable hydrophile-lipophile balance (HLB) number, which may be determined as disclosed in U.S. Pre-Grant Publication No. US2009/0047347, which is incorporated herein by reference in its entirety.

Intranasal antiviral compositions of a combination of antiviral compounds as described herein may also include flavors or scents to cover the taste of a combination of antiviral compounds as described herein. Intranasal compositions may also include isotonizing agents to make the composition isotonic. Intranasal antiviral compositions of a combination of antiviral compounds as described herein may also include stabilizing agents.

Intrapulmonary

The antiviral composition may be an intrapulmonary antiviral composition comprising a combination of antiviral compounds as described herein and at least one excipient suitable for intranasal administration. The at least one excipient suitable for intrapulmonary administration may comprise at least one compound other than water. For example, the intrapulmonary composition may comprise one or more penetration enhancers, which increase the ability of a combination of antiviral compounds as described herein to cross the pulmonary epithelia into the blood stream.

Intrapulmonary antiviral compositions may be administered to the lungs by inhalation, e.g., using an insufflator, aerosol inhaler, or a conventional or high efficiency nebulizer.

High efficiency nebulizers are inhalation devices that comprise a microperforated membrane through which a liquid solution is converted through electrical or mechanical means into aerosol droplets suitable for inhalation. High efficiency nebulizers can deliver a large fraction of a loaded dose to a patient. In some embodiments, the high efficiency nebulizer may also utilize one or more actively or passively vibrating microperforated membranes. In some embodiments, the high efficiency nebulizer may comprise one or more oscillating membranes. In some embodiments, the high efficiency nebulizer may comprise a vibrating mesh or plate with multiple apertures and optionally a vibration generator with an aerosol mixing chamber. In some such embodiments, the mixing chamber may function to collect (or stage) the aerosol from the aerosol generator.

In some embodiments, the high efficiency nebulizer may achieve lung deposition (deposited lung dose) of at least about 10% based on the nominal dose of a combination of antiviral compounds as described herein.

In some embodiments, the high efficiency nebulizer provides a combination of antiviral compounds as described herein lung deposition (deposited lung dose) of at least about 5% based on the nominal dose of a combination of antiviral compounds as described herein.

In accordance with the invention, in some embodiments, a nebulizer, such as a high efficiency nebulizer may be adapted or adaptable to operate in conjunction with a unit dosage form, such as an ampule or vial, which contains a single dose of a combination of antiviral compounds as described herein for antiviral therapy. The unit dosage form comprises a container that contains an inhalation solution comprising a combination of antiviral compounds as described herein. The container is adapted to cooperate with the high efficiency nebulizer device in such a way as to permit administration of the nominal dose of the inhalation solution to a patient in need thereof. In some embodiments, the high efficiency nebulizer and the unit dosage form are configured so that they are useable together, but not with other devices or dosage forms. In some particular embodiments, the unit dosage form is configured such that it fits into a keyhole-like structure in the high efficiency nebulizer but will not operate with other nebulizer devices. In such embodiments, the high efficiency nebulizer is configured such that it will accept and properly operate with the unit dosage form containing a combination of antiviral compounds as described herein, but not with other dosage forms.

Suitable high efficiency nebulizers with perforated membranes are disclosed in U.S. Pat. Nos. 6,962,151, 5,152,456, 5,261,601, and 5,518,179, each of which is hereby incorporated by reference in its entirety. Suitable high efficiency nebulizers contain oscillatable membranes. Features of these high efficiency nebulizers are disclosed in U.S. Pat. Nos. 7,252,085; 7,059,320; 6,983,747, each of which is hereby incorporated by reference in its entirety.

Commercial high efficiency nebulizers are available from: PARI (Germany) under the trade name eFlow®; Aerogen, Ltd. (Ireland) under the trade names AeroNeb® Go and AeroNeb® Pro, AeroNeb® Solo, and other nebulizers utilizing the OnQ® nebulizer technology; Respironics (Murrysville, Calif.) under the trade names I-Neb©; Omron (Bannockburn, Ill.) under the trade name Micro-Air®; Activaero (Germany) under the trade name Akita®, and AerovectRx (Atlanta, Ga.) under the trade name AerovectRx®.

Conventional nebulizers include, for example jet nebulizers or ultrasonic nebulizers. Jet nebulizers generally utilize compressors to generate compressed air, which breaks the liquid medication into small breathable droplets, which form an aerosolized (atomized) mist. In some of these embodiments, when the patient breathes in, a valve at the top opens, which then allows air into the apparatus, thereby speeding up the mist generation; when the patient breathes out, the top valve closes, thereby slowing down the mist generation while simultaneously permitting the patient to breathe out through the opening of a mouthpiece flap.

Some conventional nebulizers are disclosed in U.S. Pat. Nos. 6,513,727, 6,513,519, 6,176,237, 6,085,741, 6,000,394, 5,957,389, 5,740,966, 5,549,102, 5,461,695, 5,458,136, 5,312,046, 5,309,900, 5,280,784, and 4,496,086, each of which is hereby incorporated by reference in its entirety.

Commercial conventional nebulizers are available from: PARI (Germany) under the trade names PARI LC Plus®, LC Star® and PARI-Jet® A & H Products, Inc. (Tulsa, Okla.) under the trade name AquaTower®; Hudson RCI (Temecula, Calif.) under the trade name AVA-NEB®; Intersurgical, Inc. (Liverpool, N.Y.) under the trade name Cirrus®; Salter Labs (Arvin, Calif.) under the trade name Salter 8900©; Respironics (Murrysville, Pa.) under the trade name Sidestream®; Bunnell (Salt Lake City, Utah) under the trade name Whisper Jet®; Smiths-Medical (Hyth Kent, UK) under the trade name Downdraft®, and DeVilbiss (Somerset, Pa.) under the trade name DeVilbiss®.

Intravenous

The antiviral composition may be an intravenous antiviral composition comprising a combination of antiviral compounds as described herein and at least one excipient suitable for intravenous administration. The at least one excipient suitable for intravenous administration may comprise at least one compound other than water. Intravenous compositions of a combination of antiviral compounds as described herein are parenteral compositions intended for intravenous administration by injection or infusion. They may contain one or more isotonizing agents to make the compositions isotonic. They may be, and generally are, sterile, pyrogen free, or both.

Subcutaneous

The antiviral composition may be a subcutaneous antiviral composition comprising a combination of antiviral compounds as described herein and at least one excipient suitable for subcutaneous administration. The at least one excipient suitable for subcutaneous administration may comprise at least one compound other than water.

Subcutaneous compositions of a combination of antiviral compounds as described herein are parenteral compositions intended for injection under the skin. They may contain one or more isotonizing agents to make the compositions isotonic. They may be, and generally are, sterile, pyrogen free, or both.

Transdermal

The antiviral composition may be a transdermal antiviral composition comprising a combination of antiviral compounds as described herein and at least one excipient suitable for transdermal administration. The at least one excipient suitable for transdermal administration may comprise at least one compound other than water. For example, the transdermal antiviral composition may comprise one or more penetration enhancers, which increase the ability of a combination of antiviral compounds as described herein to cross the dermis into the blood stream. In addition, the transdermal composition may be delivered by a biasing mechanism, such as an iontophoresis device.

Sublingual or Buccal

The antiviral composition may be a sublingual or buccal antiviral composition comprising a combination of antiviral compounds as described herein and at least one excipient suitable for sublingual or buccal administration. The at least one excipient suitable for sublingual or buccal administration may comprise at least one compound other than water.

Intraperitoneal

The antiviral composition may be an intraperitoneal antiviral composition comprising a combination of antiviral compounds as described herein and at least one excipient suitable for intraperitoneal administration. The at least one excipient suitable for intraperitoneal administration may comprise at least one compound other than water. Intraperitoneal antiviral compositions of a combination of antiviral compounds as described herein are parenteral compositions intended for administration to the peritoneum by injection or infusion. They may contain one or more isotonizing agents to make the compositions isotonic. They may be, and generally are, sterile, pyrogen free, or both.

Intrathecal or Intracranioventricular

The antiviral composition may be an intrathecal or intracranioventricular antiviral composition comprising a combination of antiviral compounds as described herein and at least one excipient suitable for intrathecal or intracranioventricular administration. The at least one excipient suitable for intrathecal or intracranioventricular administration may comprise at least one compound other than a compound that occurs naturally with a combination of antiviral compounds as described herein in nature, e.g., water. Intrathecal or intracranioventricular antiviral compositions of a combination of antiviral compounds as described herein are parenteral compositions intended for administration into the cerebrospinal fluid administration by injection or infusion. They may contain one or more isotonizing agents to make the compositions isotonic. They may be, and generally are, sterile, pyrogen free, or both.

Other Routes of Administration

Although there have been shown and described preferred embodiments of the compositions and methods described herein, it will be readily apparent to those skilled in the art that modifications may be made thereto which do not exceed the scope of the appended claims. Therefore, the scope of the described compositions and methods is only to be limited by the following claims.

Antiviral Methods

Antiviral methods disclosed herein comprise administering an antivirally effective amount of a combination of antiviral compounds as described herein to a patient in need thereof. A patient in need of an antivirally effective amount of a combination of antiviral compounds as described herein may be a patient having, suspected of having, or being susceptible to acquiring a viral infection, including a patient having a viral infection and experiencing one or more symptoms associated with a cytokine storm, including respiratory failure, severe inflammation of the pulmonary epithelial tissue, over-production of phlegm, severe respiratory distress, reduced pulse oximetry (e.g., less than 90%, less than 85%, or less than 80% blood oxygen saturation), cardiovascular symptoms, such as congestive heart failure, renal failure, neurological pathology, sepsis, or very high or prolonged fever. A patient having a viral infection may be a patient who has been diagnosed as having a viral infection, e.g., by a competent medical professional. A patient suspected of having a viral infection may be a patient showing one or more signs or symptoms of a viral infection, such as one or more symptoms associated with a cytokine storm, for whom a diagnosis of viral infection may be tentative or not yet confirmed by definitive testing. A patient susceptible to a viral infection may be any patient whose health, environmental, behavioral or demographic condition makes the patient vulnerable to infection. A patient may belong to one or more of these categories; and the more categories to which a patient belongs, the more vulnerable the patient may be to infection. A patient whose health makes the patient vulnerable to infection may include patients who are immune compromised, of advanced or very young age, or who have one or more morbidities which make them vulnerable to infection, or if they did acquire an infection, would place them at increased risk of hospitalization, reliance on ventilation or other mechanical life support or life-saving medical intervention. A patient whose environmental or behavioral condition makes the patient more vulnerable to infection may include medical professionals, first responders, and others whose vocation or avocation increases the patient's likelihood of exposure to infection. A patient whose demographic condition makes the patient vulnerable to infection may include patients who are, based on their membership of a particular demographic group, statistically more likely to acquire an infection or to require hospitalization, reliance on ventilation or other mechanical life support or life-saving medical intervention.

Thus, an antivirally effective amount of a combination of antiviral compounds as described herein may vary depending on the patient's status. In a case in which a patient has a known viral infection, an antivirally effective amount of a combination of antiviral compounds as described herein may be an amount sufficient to reduce the patient's viral load, or to slow an increase in the patient's viral load, or to ameliorate one or more symptoms (such as one or more symptoms associated with a cytokine storm), or to improve one or more signs of viral infection in the patient. One or more symptoms of a cytokine storm include respiratory failure, severe inflammation of the pulmonary epithelial tissue, over-production of phlegm, severe respiratory distress, reduced pulse oximetry (e.g., less than 90%, less than 85%, or less than 80% blood oxygen saturation), cardiovascular symptoms, such as congestive heart failure, renal failure, neurological pathology, sepsis, or very high or prolonged fever. In a case in which a patient is suspected of having a viral infection, an antivirally effective amount of a combination of antiviral compounds as described herein may be an amount sufficient to ameliorate one or more symptoms, or to improve one or more signs of viral infection in the patient. In a case in which a patient is susceptible to acquiring a viral infection, an antivirally effective amount of a combination of antiviral compounds as described herein may be an amount sufficient to reduce the likelihood of the patient acquiring a viral infection or to reduce the severity of a viral infection if one occurs. a combination of antiviral compounds as described herein may be administered as one of the pharmaceutical compositions disclosed herein. a combination of antiviral compounds as described herein may be administered as a single therapeutic or in combination with other antiviral, palliative, or supportive therapy. A combination of antiviral compounds as described herein may be administered to patient having, or suspected of having a viral infection, such as a coronavirus infection or an influenza infection. A coronavirus infection may be an infection of SARS-CoV, MERS-CoV, SARS-CoV-2, or a corona virus associated with the common cold. An influenza infection may be caused by Influenza A virus or Influenza B virus.

A patient may be administered a therapeutically effective amount of a combination of antiviral compounds as described herein or a prophylactically effective amount of a combination of antiviral compounds as described herein, which may be administered as a pharmaceutical composition disclosed herein and may be administered as a single therapeutic agent or co-administered with another therapeutic agent. A therapeutically effective amount of a combination of antiviral compounds as described herein is an antivirally effective amount of a combination of antiviral compounds as described herein effective to treat a patient having, or suspected of having, a viral infection. A prophylactically effective amount of a combination of antiviral compounds as described herein is an antivirally effective amount of a combination of antiviral compounds as described herein effective to reduce a likelihood of a patient acquiring a viral infection or of reducing the severity of a viral infection.

In light of the disclosure herein, one skilled in the art understands how to determine an antivirally effective amount of a combination of antiviral compounds as described herein. Generally, an antivirally effective amount, a therapeutically effective amount, or a prophylactically effective amount, of a combination of antiviral compounds as described herein may be determined, e.g., by inference from in vitro testing. One skilled in the art understands that an effective dose may be inferred from the in vitro half maximal modulating (inhibitory or activating) concentration of a combination of antiviral compounds as described herein. One skilled in the art understands that the effective dose in human patients will depend on the route of administration, the pharmacokinetics, etc. Taking these factors into consideration, an antivirally effective dose of a combination of antiviral compounds as described herein may be in the range of 0.1 mg/kg to 150 mg/kg, e.g. 0.1 mg/kg to 1 mg/kg, 0.5 mg/kg to 5 mg/kg, 1 mg/kg to 10 mg/kg, 5 mg/kg to 50 mg/kg, 10 mg/kg to 100 mg/kg, or 50 mg/kg to 150 mg/kg; an effective daily dose of a combination of antiviral compounds as described herein may be some multiple of any of the values within these ranges, e.g. one to six (1 to 6) times the values within these ranges.

Transitional Phrases

In some embodiments, descriptions of the compositions and methods described herein using the transitional word "comprising" indicates that the compositions or methods are "open" to additional ingredients, components or steps. It is intended that "comprising" subsume the more limiting transitional phrases "consisting essentially of" and "consisting of." Thus, disclosure herein of matter following the transitional phrase "comprising" also fully discloses the same following the transitional phrases "consisting essentially of" or "consisting of." The transitional phrase "consisting essentially of," is of intermediate effect, indicating that the subject matter that follows consists only of the recited elements and such additional matter as does not materially affect the novel and basic properties of the claim or claim element. The transitional phrase "consisting of," indicates that the subject matter that follows is limited to the recited steps or ingredients and is closed to other steps or ingredients not recited. Where a transitional phrase appears within a clause or a sub-clause following another transitional phrase, it is intended that the embedded transitional phrase affect only the phrase in which it appears.

EXAMPLES

Pharmaceutical compositions and antiviral methods disclosed herein may be further understood with reference to the following examples.

COMPARATIVE EXAMPLES

Comparative Example 1: In Vitro Antiviral Activity of Comparative Compounds

The in vitro antiviral (SARS-CoV-2) activities of Calpain Inhibitor IV, hydroxychloroquine, chloroquine, E64d (aloxistatin) and remdesivir (comparative compounds) were determined by a cell viability assay. To determine virus inhibition, VERO-E6 cells enriched for angiotensin converting enzyme 2 receptor (ACE-2) were plated into a 384 well titer plate along with SARS-CoV-2 virus. Medium (control) or comparative control in medium (experimental) at various concentrations was added to wells. Medium-only wells (no cells) were used as controls to determine background luminescence. Cell viability in the presence of SARS-CoV-2 was quantified using the CellTiter-Glo® cell viability assay (Promega, Madison, WI) according to manufacturer's recommendations, converting luminescence values to cell numbers according to a standard curve. Toxicity for each comparative compound was determined by similar methods in the absence of SARS-CoV-2 virus. Table I provides the in vitro activity ($IC_{50}$) and toxicity ($CC_{50}$) results for each compound.

TABLE I

In Vitro Anti-SARS-CoV-2 Activity of Positive Controls

| Compound | $IC_{50}$ (μM) | $CC_{50}$ (μM) |
|---|---|---|
| Calpain Inhibitor IV | 0.12 | >7.17 |
| Hydroxychloroquine | 3.53 | >30.00 |
| Chloroquine | 3.78 | >30.00 |
| E64d (aloxistatin) | 7.48 | >30.00 |
| Remdesivir | 11.48 | >30.00 |

Comparative Example 2: In Vitro Activity of penta-O-galloyl-β-D-glucose

The in vitro immune modulating effects of penta-O-galloyl-β-D-glucose were tested in the presence of SARS-CoV-2 in lung epithelial cells or macrophages treated with SARS-CoV-2 Spike protein. To determine immune modulation, the methods of Yong, "Cytokine Multiplex Analysis," Methods Mol. Biol. 2009; 511: 85-105 (July 2019), particularly the PCR and Luminex™ methods, were employed to determine the effect of penta-O-galloyl-β-D-glucose on expression of cytokines in the macrophages treated with SARS-CoV-2 Spike protein. The Luminex™ method was effected using a Human Cytokine Magnetic 35-Plex Panel ("35-Plex Panel"), from Invitrogen. The 35-Plex Panel can measure expression of 35 cytokines in various sample types: EGF, Eotaxin, FGF basic, G-CSF, GM-CSF, HGF, IFN-α, IFN-γ, IL-1ra, IL-1α, IL-1β, IL-2, IL-2r, IL-3, IL-4, IL-5, IL-6, IL-7, IL-8, IL-9, IL-10, IL-12 (p40/p70), IL-13, IL-15, IL-17A, IL-17F, IL-22, IP-10, MCP-1, MIG, MIP-1α, MIP-1β, RANTES, TNF-α, and VEGF in various sample types. The immune modulator, penta-O-galloyl-β-D-glucose hydrate inhibited expression of pro-inflammatory cytokines IL-1a, VEGF, IL-1β, IL-2, IL-4, IL-5, IL-6, IL-8, IL-12p70, IL-13, GM-CSF, GRO, MCP-1, MIP-1α, MIP-1p, MMP-9, RANTES, and TNF-α in macrophages treated with Spike protein. The immune modulator penta-O-galloyl-β-D-glucose hydrate activated expression of cytokine modulators IL-10 and IFN-γ in macrophages treated with Spike protein. However, penta-O-galloyl-β-D-glucose hydrate was not observed to induce apoptosis in macrophages treated with SARS-CoV-2 spike protein by caspase 3 activation. Based on these results, penta-O-galloyl-β-D-glucose hydrate was identified as a potent modulator of SARS-CoV-2 Spike protein-induced pro-inflammatory cytokines and is expected to have similar activity in vivo.

Comparative Example 3: In Vitro Activity of Tetrandrine

The in vitro activity of tetrandrine against SARS-CoV-2, the virus that causes COVID-19, was tested in a cell viability assay. To determine virus inhibition, VERO-E6 cells enriched for angiotensin converting enzyme 2 receptor (ACE-2) were plated into a 384 well titer plate along with SARS-CoV-2 virus. Medium (control) or tetrandrine in medium (experimental) at various concentrations was added to wells. Medium-only wells (no cells) were used as controls to determine background luminescence. Cell viability in the presence of SARS-CoV-2 was quantified using the CellTiter-Glo® cell viability assay (Promega, Madison, WI) according to manufacturer's recommendations, converting luminescence values to cell numbers according to a standard curve. The graph in FIG. 1 shows the results of this assay for SARS-CoV-2.

FIG. 1 shows curve representing the percent maximum inhibition versus tetrandrine concentration. The $IC_{50}$ for tetrandrine was determined to be 1.25 μM.

To determine tetrandrine toxicity, VERO-E6 cells enriched for angiotensin converting enzyme 2 receptor (ACE-2) were plated into a 384 well titer plate in the absence of virus. Medium (control) or tetrandrine in medium (experimental) at various concentrations was added to wells. Medium-only wells (no cells) were used as controls to determine background luminescence. Cell viability in the absence of virus was quantified using the CellTiter-Glo® cell viability assay (Promega, Madison, WI) according to manufacturer's recommendations, converting luminescence values to cell numbers according to a standard curve. The $CC_{50}$ was determined to be 6.28 μM. The graph in FIG. 2 shows the results of the toxicity assay.

FIG. 2 shows the tetrandrine toxicity curve. Tetrandrine had a $CC_{50}$ value of 6.28 μM. As can be seen by comparing the $IC_{50}$ and $CC_{50}$ values of tetrandrine with those of the compounds tested in Comparative Example 1, tetrandrine has favorable in vitro antiviral activity against SARS-CoV-2 and favorable in vitro toxicity.

Comparative Example 4: In Vitro Activity of Cepharanthine

The in vitro activity of cepharanthine against SARS-CoV-2, the virus that causes COVID-19, was tested in a cell viability assay. To determine virus inhibition, VERO-E6 cells enriched for angiotensin converting enzyme 2 receptor (ACE-2) were plated into a 384 well titer plate along with SARS-CoV-2 virus. Medium (control) or cepharanthine in medium (experimental) at various concentrations was added to wells. Medium-only wells (no cells) were used as controls to determine background luminescence. Cell viability in the presence of SARS-CoV-2 was quantified using the CellTiter-Glo® cell viability assay (Promega, Madison, WI) according to manufacturer's recommendations, converting luminescence values to cell numbers according to a standard curve. The graph in FIG. 3 shows the results of this assay for SARS-CoV-2.

FIG. 3 shows the curve of the percent maximum inhibition versus cepharanthine concentration. The $IC_{50}$ for cepharanthine was determined to be 0.51 μM.

To determine cepharanthine toxicity, VERO-E6 cells enriched for angiotensin converting enzyme 2 receptor (ACE-2) were plated into a 384 well titer plate in the absence of virus. Medium (control) or cepharanthine in medium (experimental) at various concentrations was added to wells. Medium-only wells (no cells) were used as controls to determine background luminescence. Cell viability in the absence of virus was quantified using the CellTiter-Glo® cell viability assay (Promega, Madison, WI) according to manufacturer's recommendations, converting luminescence values to cell numbers according to a standard curve. The $CC_{50}$ was determined to be 7.22 μM. The graph in FIG. 4 shows the results of the toxicity assay.

FIG. 4 shows the cepharanthine toxicity curve. As can be seen by comparing the $IC_{50}$ and $CC_{50}$ values of cepharanthine with those of the compounds tested in Comparative Example 1, cepharanthine has favorable in vitro antiviral activity against SARS-CoV-2 and favorable in vitro toxicity.

WORKING EXAMPLES

Example 1: Synergistic Activity of Tetrandrine and Cepharanthine

The anti-viral activity of tetrandrine (IATAV049) and cepharanthine (IATAV51) were assessed in the CPE assay on VERO-E6 cells enriched with ACE2 receptors, infected with the whole SARS-CoV-2 virus, as described above in Comparative Examples 1-3. The half maximal effective concentration ($EC_{50}$), fifty percent cytotoxic concentration ($CC_{50}$), and selectivity index (SI; $CC_{50}/EC_{50}$) were determined for tetrandrine and cepharanthine separately and in combination. The following results were obtained.

| | | | |
|---|---|---|---|
| Tetrandrine: | $EC_{50}$: 1.25 μM | $CC_{50}$: 6.28 μM | SI: 5.02. |
| Cepharanthine | $EC_{50}$: 510 nM | $CC_{50}$: 7.22 μM | SI: 14.16. |

When tetrandrine is combined with cepharanthine:

$EC_{50}$ of tetrandrine required is 200.2 nM, 6.24-fold lower than when used alone.

$CC_{50}$ of tetrandrine is >12.04 μM.

When cepharanthine is combined with tetrandrine:

$EC_{50}$ of cepharanthine is 16.64 nM, 30.64-fold lower than when used alone.

$CC_{50}$ of cepharanthine required is >12.04 μM.

Conclusions: (1) the combination of tetrandrine and cepharanthine shows clear synergism across a broad range of dose combinations, and (2) the toxicity of the combination is lower than each alone.

Figure 6:
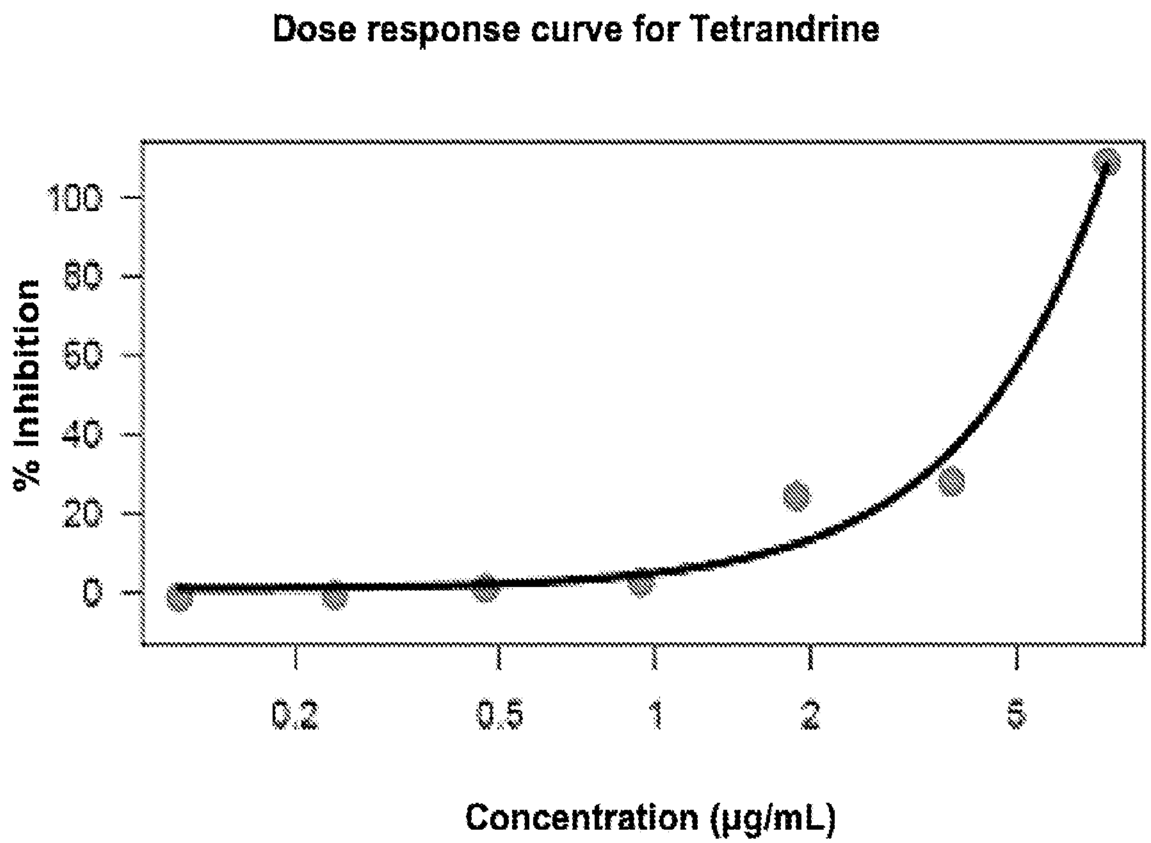
FIG. 6 is a dose-response curve for cepharanthine in VERO-E6 cells enriched in ACE-2 receptor and infected with SARS-CoV-2 virus.
Figure 7:
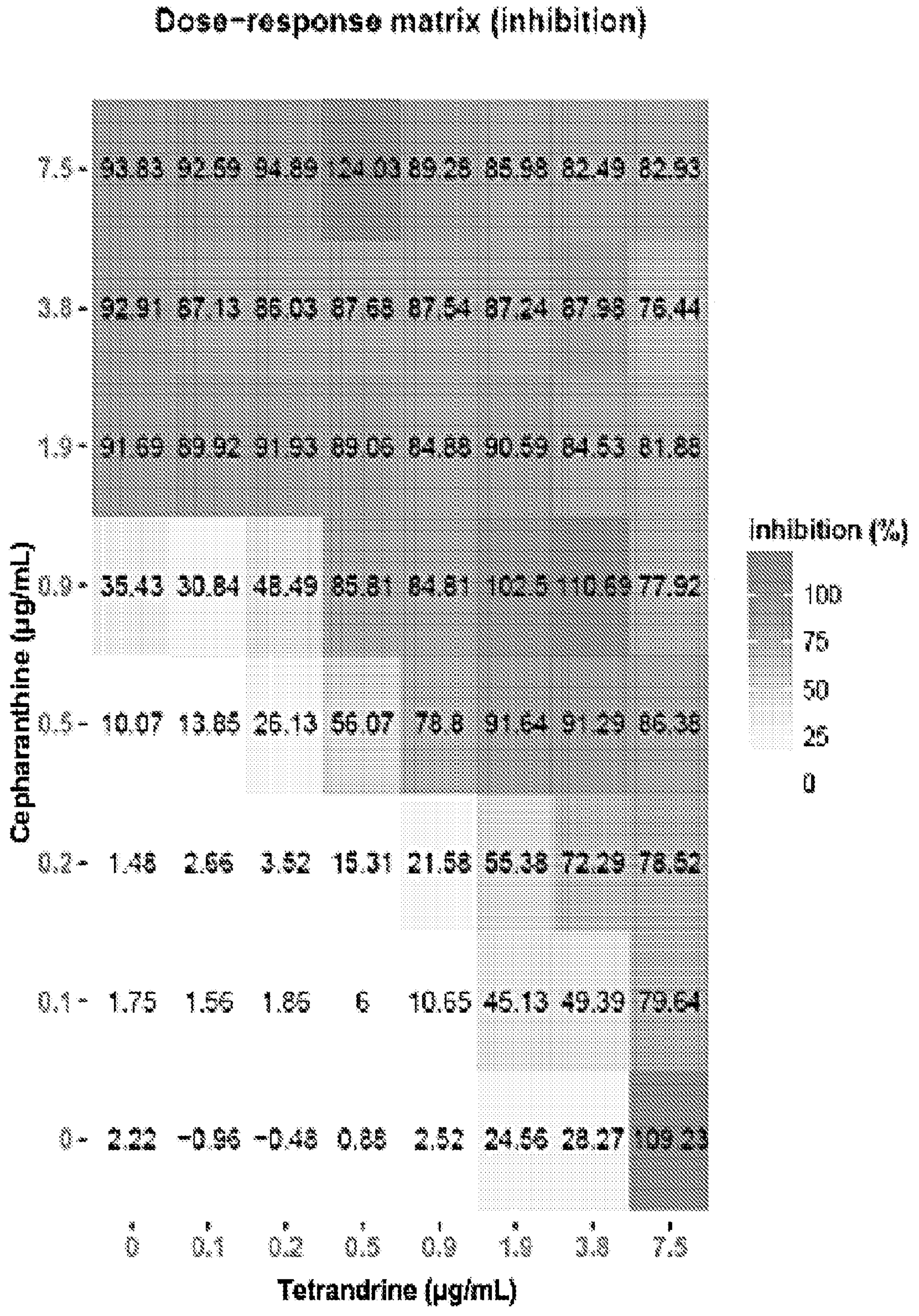
FIG. 7 is a dose-response matrix for tetrandrine and cepharanthine in VERO-E6 cells enriched in ACE-2 receptor and infected with SARS-CoV-2 virus.
Figure 8:
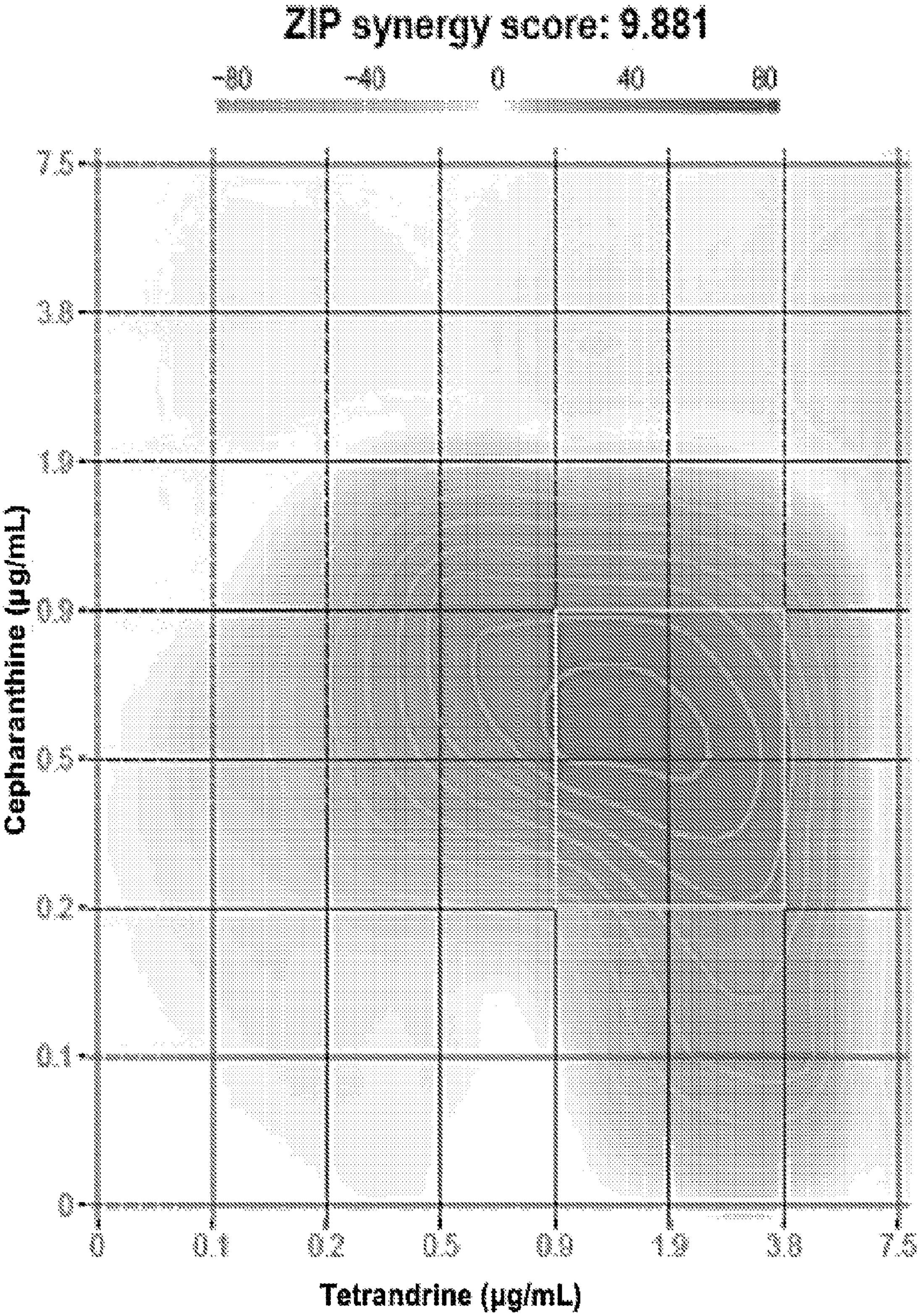
FIG. 8 is a 2D heat map representation of zero interaction potency (ZIP) synergy score for the combination of tetrandrine and cepharanthine in SARS-CoV-2 infected VERO-E6 cells enriched in ACE-2 receptor.

FIGS. 5-9 show the synergism of tetrandrine and cepharanthine in VeroE6 cells infected with SARS-CoV-2 cells. FIGS. 5 and 6 show the dose response activity curves for the individual compounds. FIG. 7 is a heat map of dose response matrix of inhibition of SARS-CoV-2 infection. FIG. 8 shows the zero interaction potency (ZIP) synergy score.

Figure 9:
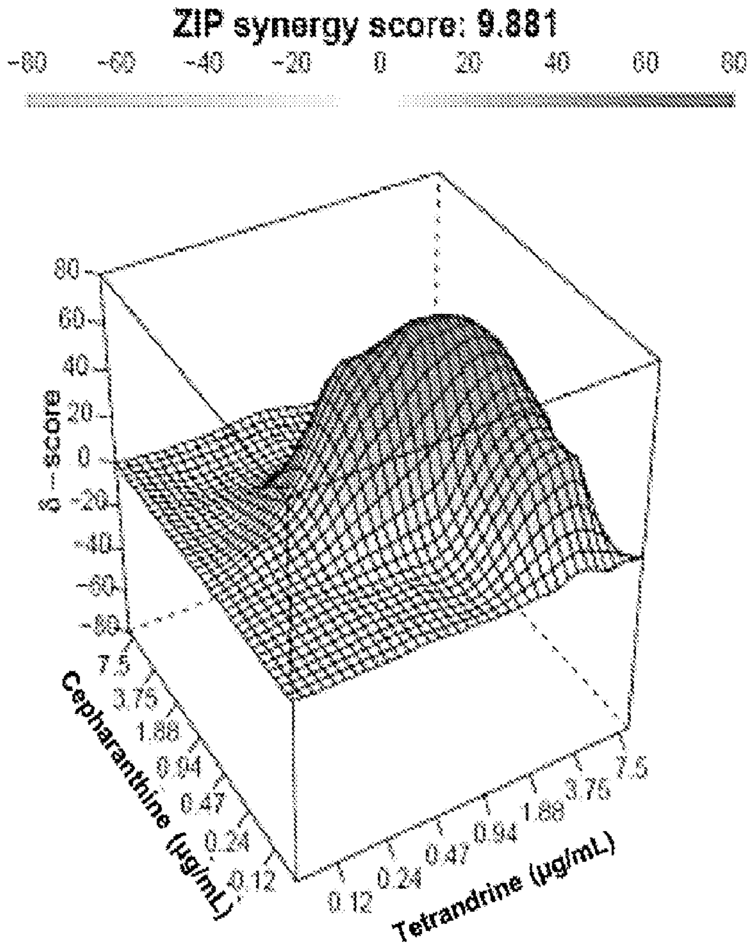
FIG. 9 is a 3D heat map representation of zero interaction potency (ZIP) synergy score for the combination of tetrandrine and cepharanthine in SARS-CoV-2 infected VERO-E6 cells enriched in ACE-2 receptor.

FIG. 9 is a 3D representation of the total ZIP score for the compounds.

ZIP (zero interaction potency) synergy score for all doses=9.88.

Total Inhibition of cell death (100% death inhibition).

Large area of interaction (across multiple doses).

ZIP score in most synergistic area 48.71.

Example 2: Synergistic Activity of Tetrandrine, Cepharanthine and Penta-O-Galloyl-β-D-Glucose Combination 1 is composed of 3 compounds: two designated herein as antiviral compounds, of which one, cepharanthine is an entry inhibitor and the other, tetrandrine is a proteolytic processing inhibitor of S1/S2 site. When employed together their SARS-CoV-2 inhibitory activity increases thirty-fold (30×) compared to each alone. The immune modulator, penta-O-galloyl-β-glucose hydrate is a MyD88 inhibitor, resulting in inhibition of pro-inflammatory pathways (IRAK1, NF-kB and MAPK), while increasing expression of IRAK4, thereby increasing Type 1 Interferon response. Penta-O-galloyl-β-glucose hydrate effect results in the suppression of multiple pro-inflammatory cytokines (IL-1β, TNF-α, IL-6 IL-8, IL-12, MCP-1 and MIP-1α), while increasing expression of the anti-inflammatory cytokine IL-10. The combination of the three compounds results in the induction of programmed cell death (apoptosis) in infected macrophages.

Combination 1, therefore, utilizes antiviral (AV) and immune modulating (IM) compounds that are selectively active during viral infection (AVIM). Combination 1 neutralizes the virus and modulate the host immune response to prevent cytokine storm and macrophage activation syndrome while increasing the innate Type 1 interferon response. Combination 1 promises applicability not only to the current pandemic, but also future, novel coronavirus strains, tempering the emergence of a future pandemic wave.

Combination 1 comprises antiviral compounds tetrandrine and cepharanthine and immune modulator penta-O-galloyl-β-glucose hydrate in various ratios. In some embodiments, the ratio of combination is tetrandrine, cepharanthine and penta-O-galloyl-β-glucose hydrate, about 2:1:10, respectively.

Example 3: Antiviral Treatment with a Combination of Tetrandrine and Cepharanthine Patients having, or suspected of having, viral infections with SARS-COV, SARS-COV-2, common cold coronavirus, Influenza A or Influenza B and having, or judged by a medical professional of being in danger of developing, one or more symptoms associated with a cytokine storm caused, or suspected of being caused, by a virus, are administered 0.1 mg to 100 mg of each of tetrandrine and cepharanthine one to six times daily. The combination of tetrandrine and cepharanthine antiviral compound as described herein is administered by intranasal, pulmonary, oral, or intravenous route.

Example 4: Antiviral Treatment with an Immune Modulator

Patients having, or suspected of having, viral infections with SARS-COV, SARS-COV-2, common cold coronavirus, Influenza A or Influenza B and having, or judged by a medical professional of being in danger of developing, one or more symptoms associated with a cytokine storm caused, or suspected of being caused, by a virus, are administered 0.1 mg to 100 mg of a combination of antiviral compounds and one or more immune modulators as described herein one to six times daily. A combination of antiviral compounds and at least one immune modulator, as described herein, is administered by intranasal, pulmonary, oral, or intravenous route. In some embodiments, the immune modulator comprises tetrandrine, cepharanthine, penta-O-galloyl-β-D-glucose hydrate.

While a number of embodiments of pharmaceutical compositions and antiviral methods are described herein, one skilled in the art understand that the examples may be altered to provide other embodiments that utilize a combination of antiviral compounds as described herein compositions and methods described herein. Therefore, it will be appreciated that the scope of this invention is to be defined by the appended claims rather than by the specific embodiments that have been represented by way of example.

What is claimed is:

1. An antiviral method of treating a patient in need thereof, the method comprising administering to the patient in need thereof an antiviral composition comprising:

(a) a pharmaceutically acceptable excipient;

(b) a first antiviral compound comprising tetrandrine, an antiviral salt, a hydrate, or an anhydrate thereof;

(c) a second antiviral compound comprising cepharanthine, an antiviral salt, a hydrate, or an anhydrate thereof; and (d) an immune modulator comprising penta-O-galloyl-β-glucose hydrate, an antiviral salt, a hydrate, or an anhydrate thereof; wherein the antiviral composition is pharmaceutically effective to treat a virus infection.

2. The method of claim 1, wherein the patient has, is suspected of having, or is susceptible to a coronavirus infection or an influenza virus infection.

3. The method of claim 2, wherein the patient has, is suspected of having, or is susceptible to a coronavirus infection, wherein the coronavirus is, or is suspected of being, a SARS-CoV, a MERS-CoV, or a common cold coronavirus.

4. The method of claim 2, wherein the patient has, is suspected of having, or is susceptible to an influenza virus infection, wherein the influenza virus causing or suspected of causing the infection is an influenza A virus or an influenza B virus.

5. The method of claim 1, wherein the method comprises orally administering the antiviral composition to the patient in need thereof.

* * * * *